(12) United States Patent
Jain et al.

(10) Patent No.: US 6,316,029 B1
(45) Date of Patent: Nov. 13, 2001

(54) RAPIDLY DISINTEGRATING SOLID ORAL DOSAGE FORM

(75) Inventors: Rajeev A. Jain, Norristown; Stephen B. Ruddy, Schwenksville, both of PA (US); Kenneth Iain Cumming, Phibsoboro (GB); Maurice Joseph Anthony Clancy, Dublin; Janet Elizabeth Codd, Athlone, both of (IE)

(73) Assignee: Flak Pharma International, Ltd., Shannon (IL)

( * ) Notice: Subject to any disclaimer, the term of this patent is extended or adjusted under 35 U.S.C. 154(b) by 0 days.

(21) Appl. No.: 09/572,961

(22) Filed: May 18, 2000

(51) Int. Cl.[7] ............... A61K 9/14; A61K 9/00; A61K 9/50

(52) U.S. Cl. ............ 424/484; 424/489; 424/488; 424/484; 424/400; 424/501; 424/486

(58) Field of Search ............ 424/501, 439, 424/489, 494, 484, 442, 485, 488, 400, 426, 486, 428, 429

(56) References Cited

U.S. PATENT DOCUMENTS

| | | |
|---|---|---|
| 4,178,695 | 12/1979 | Erbeia ........................ 34/5 |
| 4,616,047 | 10/1986 | Lafon ........................ 523/105 |
| 4,642,903 | 2/1987 | Davies ........................ 34/5 |
| 5,073,374 | 12/1991 | McCarty ........................ 424/435 |
| 5,112,616 | 5/1992 | McCarty ........................ 424/435 |
| 5,145,684 * | 9/1992 | Liversidge et al. ........................ 424/489 |
| 5,178,878 | 1/1993 | Wehling et al. ........................ 424/466 |
| 5,188,825 | 2/1993 | Iles et al. ........................ 424/78.1 |
| 5,219,574 | 6/1993 | Wehling et al. ........................ 424/464 |
| 5,223,264 | 6/1993 | Wehling et al. ........................ 424/466 |
| 5,318,767 | 6/1994 | Liversidge et al. ........................ 424/4 |
| 5,384,124 | 1/1995 | Courteille et al. ........................ 424/430 |
| 5,399,363 | 3/1995 | Liversidge et al. ........................ 424/490 |
| 5,401,513 | 3/1995 | Wehling et al. ........................ 424/464 |
| 5,429,824 | 7/1995 | June ........................ 424/489 |
| 5,446,464 | 8/1995 | Feldle ........................ 342/175 |
| 5,464,632 | 11/1995 | Cousin et al. ........................ 424/465 |
| 5,494,683 | 2/1996 | Liversidge et al. ........................ 424/490 |
| 5,503,846 | 4/1996 | Wehling et al. ........................ 424/466 |
| 5,510,118 | 4/1996 | Bosch et al. ........................ 424/489 |
| 5,518,187 | 5/1996 | Bruno et al. ........................ 241/5 |
| 5,518,738 | 5/1996 | Eickhoff et al. ........................ 424/493 |
| 5,552,160 | 9/1996 | Liversidge et al. ........................ 424/489 |
| 5,567,439 | 10/1996 | Myers et al. ........................ 424/486 |
| 5,576,014 | 11/1996 | Mizumoto et al. ........................ 424/435 |
| 5,587,172 | 12/1996 | Cherukuri et al. ........................ 424/401 |
| 5,587,180 | 12/1996 | Allen, Jr. et al. ........................ 424/499 |
| 5,591,456 * | 1/1997 | Franson et al. ........................ 424/494 |
| 5,595,761 | 1/1997 | Allen, Jr. et al. ........................ 424/484 |
| 5,607,697 | 3/1997 | Alkire et al. ........................ 424/495 |
| 5,622,719 | 4/1997 | Myers et al. ........................ 424/488 |
| 5,631,023 | 5/1997 | Kearney et al. ........................ 424/465 |
| 5,635,210 | 6/1997 | Allen, Jr. et al. ........................ 424/465 |
| 5,639,475 | 6/1997 | Bettman et al. ........................ 424/466 |
| 5,709,886 | 1/1998 | Bettman et al. ........................ 424/495 |

(List continued on next page.)

FOREIGN PATENT DOCUMENTS

WO 98/14179    4/1998  (WO).
WO 98/46215   10/1998  (WO).

*Primary Examiner*—Thurman K. Page
*Assistant Examiner*—Blessing Fubara
(74) *Attorney, Agent, or Firm*—Foley & Lardner

(57) ABSTRACT

Disclosed is a rapidly disintegrating solid oral dosage form of a poorly soluble active ingredient and at least one pharmaceutically acceptable water-soluble or water-dispersible excipient, wherein the poorly soluble active ingredient particles have an average diameter, prior to inclusion in the dosage form, of less than about 2000 nm. The dosage form of the invention has the advantage of combining rapid presentation and rapid dissolution of the active ingredient in the oral cavity.

70 Claims, 2 Drawing Sheets

U.S. PATENT DOCUMENTS

| | | | |
|---|---|---|---|
| 5,718,388 | 2/1998 | Czekai et al. | 241/21 |
| 5,747,001 | 5/1998 | Wiedmann et al. | 424/45 |
| 5,753,254 * | 5/1998 | Khan et al. | 424/439 |
| 5,776,491 | 7/1998 | Allen, Jr. et al. | 424/465 |
| 5,807,576 | 9/1998 | Allen et al. | 424/465 |
| 5,807,577 | 9/1998 | Ouali | 424/466 |
| 5,807,578 | 9/1998 | Acosta-Cuello et al. | 424/466 |
| 5,827,541 | 10/1998 | Yarwood et al. | 424/489 |
| 5,851,553 | 12/1998 | Myers et al. | 424/488 |
| 5,862,999 | 1/1999 | Czekai et al. | 241/21 |
| 5,866,163 | 2/1999 | Myers et al. | 424/469 |
| 5,869,098 | 2/1999 | Misra et al. | 424/484 |
| 5,871,781 | 2/1999 | Myers et al. | 425/9 |
| 5,972,389 * | 10/1999 | Shell et al. | 424/501 |

* cited by examiner

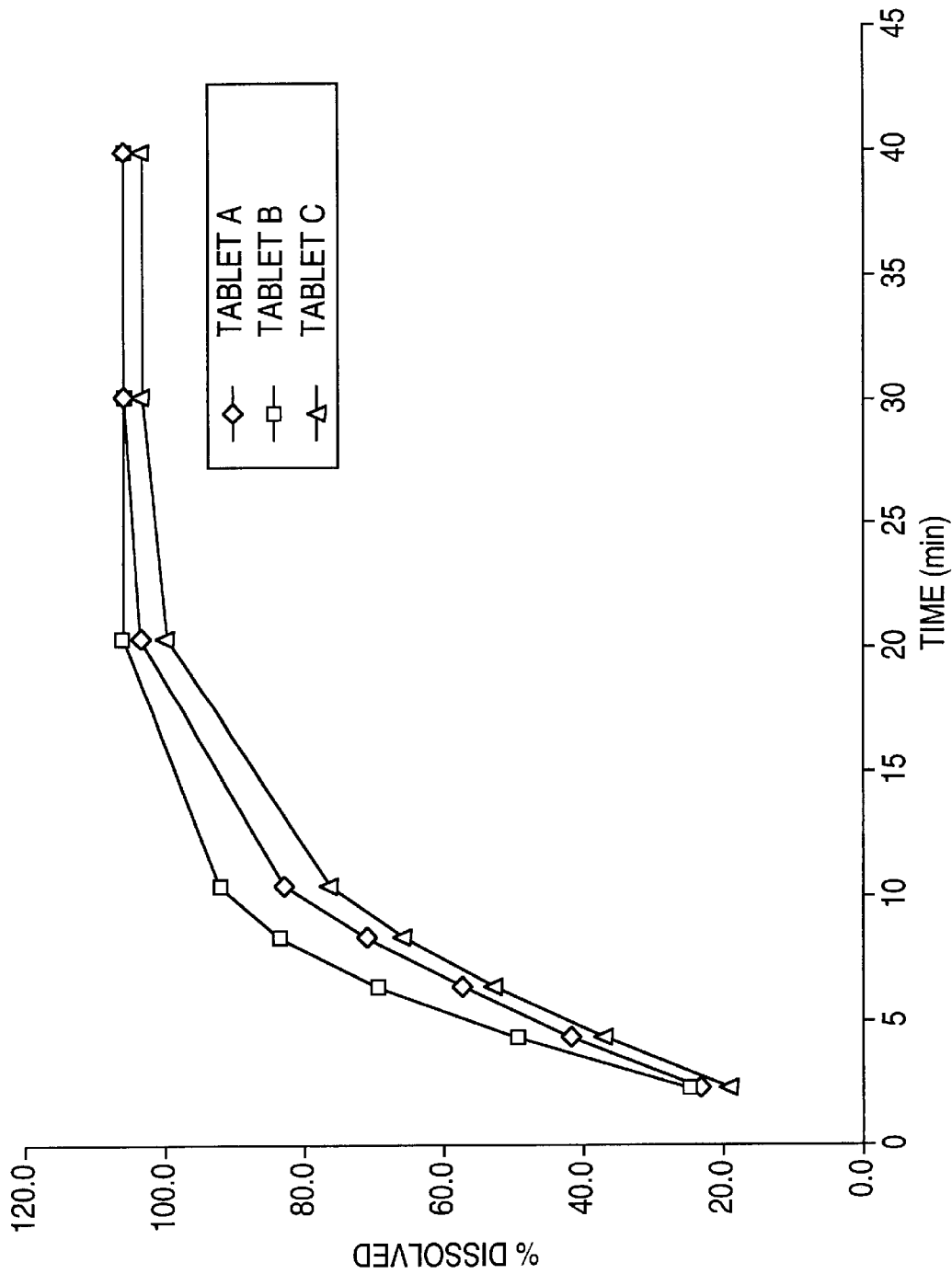

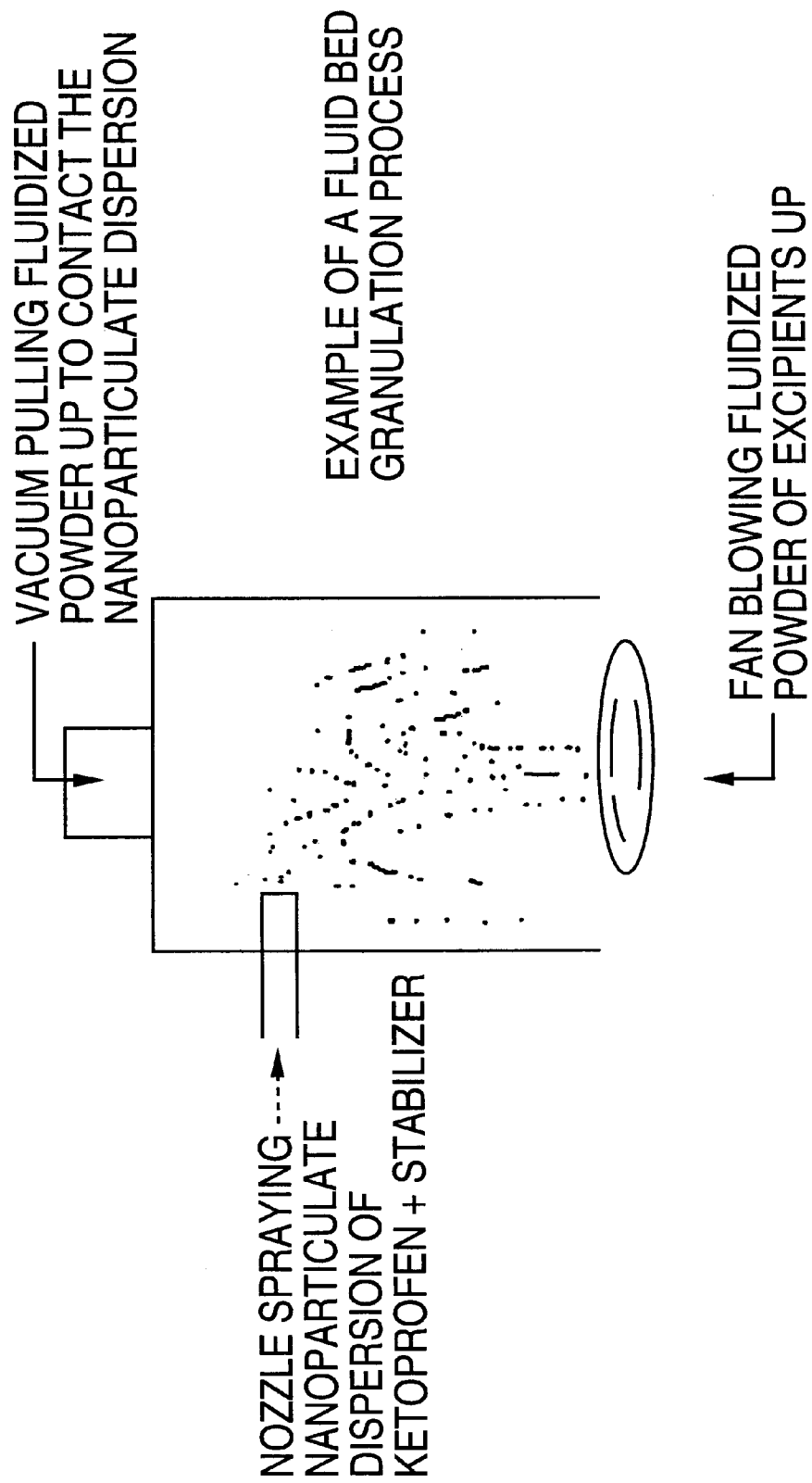

RAPIDLY DISINTEGRATING SOLID ORAL DOSAGE FORM

FIELD OF THE INVENTION

The present invention relates to a rapidly disintegrating or dissolving solid oral dosage form comprising a poorly soluble, nanoparticulate active ingredient.

BACKGROUND OF THE INVENTION

Nanoparticulate compositions, first described in U.S. Pat. No. 5,145,684 ("the '684 patent"), are particles consisting of a poorly soluble active agent having adsorbed onto the surface thereof a non-crosslinked surface stabilizer. The '684 patent also describes methods of making such nanoparticulate compositions. Nanoparticulate compositions are desirable because with a decrease in particle size, and a consequent increase in surface area, a composition is rapidly dissolved and absorbed following administration. Methods of making such compositions are described in U.S. Pat. Nos. 5,518,187 and 5,862,999, both for "Method of Grinding Pharmaceutical Substances," U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described in, for example, U.S. Pat. No. 5,318,767 for "X-Ray Contrast Compositions Useful in Medical Imaging;" U.S. Pat. Nos. 5,399,363 and 5,494,683 for "Surface Modified Anticancer Nanoparticles;"U.S. Pat. No. 5,429,824 for "Use of Tyloxapol as a Nanoparticulate Stabilizer;" U.S. Pat. No. 5,518,738 for "Nanoparticulate NSAID Formulations;" U.S. Pat. No. 5,552,160 for "Surface Modified NSAID Nanoparticles;" and U.S. Pat. No. 5,747,001 for "Aerosols Containing Beclomethasone Nanoparticle Dispersions." None of these references, or any other reference that describes nanoparticulate compositions, relates to a rapidly disintegrating or dissolving solid oral dosage form containing a nanoparticulate active ingredient.

Current manufacturers of rapidly disintegrating or dissolving solid dose oral formulations include Cima Labs, Fuisz Technologies Ltd., Prographarm, R. P. Scherer, and Yamanouchi-Shaklee. All of these manufacturers market different types of rapidly dissolving solid oral dosage forms.

Cima Labs markets OraSolv®, which is an effervescent direct compression tablet having an oral dissolution time of five to thirty seconds, and DuraSolv®, which is a direct compression tablet having a taste-masked active agent and an oral dissolution time of 15 to 45 seconds. Cima's U.S. Pat. No. 5,607,697, for "Taste Masking Microparticles for Oral Dosage Forms," describes a solid dosage form consisting of coated microparticles that disintegrate in the mouth. The microparticle core has a pharmaceutical agent and one or more sweet-tasting compounds having a negative heat of solution selected from mannitol, sorbitol, a mixture of an artificial sweetener and menthol, a mixture of sugar and menthol, and methyl salicylate. The microparticle core is coated, at least partially, with a material that retards dissolution in the mouth and masks the taste of the pharmaceutical agent. The microparticles are then compressed to form a tablet. Other excipients can also be added to the tablet formulation.

WO 98/46215 for "Rapidly Dissolving Robust Dosage Form," assigned to Cima Labs, is directed to a hard, compressed, fast melt formulation having an active ingredient and a matrix of at least a non-direct compression filler and lubricant. A non-direct compression filler is typically not free-flowing, in contrast to a direct compression (DC grade) filler, and usually requires additionally processing to form free-flowing granules.

Cima also has U.S. patents and international patent applications directed to effervescent dosage forms (U.S. Pat. Nos. 5,503,846, 5,223,264, and 5,178,878) and tableting aids for rapidly dissolving dosage forms (U.S. Pat. Nos. 5,401,513 and 5,219,574), and rapidly dissolving dosage forms for water soluble drugs (WO 98/14179 for "Taste-Masked Microcapsule Composition and Methods of Manufacture").

Fuisz Technologies, now part of BioVail, markets Flash Dose®, which is a direct compression tablet containing a processed excipient called Shearform®. Shearform® is a cotton candy-like substance of mixed polysaccharides converted to amorphous fibers. U.S. patents describing this technology include U.S. Pat. No. 5,871,781 for "Apparatus for Making Rapidly Dissolving Dosage Units;" U.S. Pat. No. 5,869,098 for "Fast-Dissolving Comestible Units Formed Under High-Speed/High-Pressure Conditions;" U.S. Pat. Nos. 5,866,163, 5,851,553, and 5,622,719, all for "Process and Apparatus for Making Rapidly Dissolving Dosage Units and Product Therefrom;" U.S. Pat. No. 5,567,439 for "Delivery of Controlled-Release Systems;" and U.S. Pat. No. 5,587,172 for "Process for Forming Quickly Dispersing Comestible Unit and Product Therefrom."

Prographarm markets Flashtab®, which is a fast melt tablet having a disintegrating agent such as carboxymethyl cellulose, a swelling agent such as a modified starch, and a taste-masked active agent. The tablets have an oral disintegration time of under one minute (U.S. Pat. No. 5,464,632).

R. P. Scherer markets Zydis®, which is a freeze-dried tablet having an oral dissolution time of 2 to 5 seconds. Lyophilized tablets are costly to manufacture and difficult to package because of the tablets sensitivity to moisture and temperature. U.S. Pat. No. 4,642,903 (R. P. Scherer Corp.) refers to a fast melt dosage formulation prepared by dispersing a gas throughout a solution or suspension to be freeze-dried. U.S. Pat. No. 5,188,825 (R. P. Scherer Corp.) refers to freeze-dried dosage forms prepared by bonding or complexing a water-soluble active agent to or with an ion exchange resin to form a substantially water insoluble complex, which is then mixed with an appropriate carrier and freeze dried. U.S. Pat. No. 5,631,023 (R. P. Scherer Corp.) refers to freeze-dried drug dosage forms made by adding xanthan gum to a suspension of gelatin and active agent. U.S. Pat. No. 5,827,541 (R. P. Scherer Corp.) discloses a process for preparing solid pharmaceutical dosage forms of hydrophobic substances. The process involves freeze-drying a dispersion containing a hydrophobic active ingredient and a surfactant, in a non-aqueous phase; and a carrier material, in an aqueous phase.

Yamanouchi-Shaklee markets Wowtab®, which is a tablet having a combination of a low moldability and a high moldability saccharide. U.S. Patents covering this technology include U.S. Pat. No. 5,576,014 for "Intrabuccally Dissolving Compressed Moldings and Production Process Thereof," and U.S. Pat. No. 5,446,464 for "Intrabuccally Disintegrating Preparation and Production Thereof."

Other companies owning rapidly dissolving technology include Janssen Pharmaceutica. U.S. patents assigned to Janssen describe rapidly dissolving tablets having two polypeptide (or gelatin) components and a bulking agent, wherein the two components have a net charge of the same sign, and the first component is more soluble in aqueous solution than the second component. See U.S. Pat. No.

5,807,576 for "Rapidly Dissolving Tablet;" U.S. Pat. No. 5,635,210 for "Method of Making a Rapidly Dissolving Tablet;" U.S. Pat. No. 5,595,761 for "Particulate Support Matrix for Making a Rapidly Dissolving Tablet;" U.S. Pat. No. 5,587,180 for "Process for Making a Particulate Support Matrix for Making a Rapidly Dissolving Tablet;" and U.S. Pat. No. 5,776,491 for "Rapidly Dissolving Dosage Form."

Eurand America, Inc. has U.S. patents directed to a rapidly dissolving effervescent composition having a mixture of sodium bicarbonate, citric acid, and ethylcellulose (U.S. Pat. Nos. 5,639,475 and 5,709,886).

L.A.B. Pharmaceutical Research owns U.S. patents directed to effervescent-based rapidly dissolving formulations having an effervescent couple of an effervescent acid and an effervescent base (U.S. Pat. Nos. 5,807,578 and 5,807,577).

Schering Corporation has technology relating to buccal tablets having an active agent, an excipient (which can be a surfactant) or at least one of sucrose, lactose, or sorbitol, and either magnesium stearate or sodium dodecyl sulfate (U.S. Pat. Nos. 5,112,616 and 5,073,374).

Laboratoire L. LaFon owns technology directed to conventional dosage forms made by lyophilization of an oil-in-water emulsion in which at least one of the two phases contains a surfactant (U.S. Pat. No. 4,616,047). For this type of formulation, the active ingredient is maintained in a frozen suspension state and is tableted without micronization or compression, as such processes could damage the active agent.

Finally, Takeda Chemicals Inc., Ltd. owns technology directed to a method of making a fast dissolving tablet in which an active agent and a moistened, soluble carbohydrate are compression molded into a tablet, followed by drying of the tablets.

None of the described prior art teaches a rapidly disintegrating or dissolving, or "fast melt," dosage form in which a poorly soluble active ingredient is in a nanoparticulate form. This is significant because the prior art fast melt formulations do not address the problems associated with the bioavailability of poorly soluble drugs. While prior art fast melt dosage forms may provide rapid presentation of a drug, frequently there is an undesirable lag in the onset of therapeutic action because of the poor solubility and associated slow dissolution rate of the drug. Thus, while prior art fast melt dosage forms may exhibit rapid disintegration of the drug carrier matrix, this does not result in rapid dissolution and absorption of the poorly soluble drug contained within the dosage form.

There is a need in the art for rapidly disintegrating or dissolving dosage forms having rapid onset of action for poorly soluble drugs. The present invention satisfies this need.

SUMMARY OF THE INVENTION

This invention is directed to the surprising and unexpected discovery of new rapidly disintegrating or dissolving solid dose oral formulations of nanoparticulate compositions of poorly soluble drugs. The rapidly disintegrating or dissolving solid dose oral formulations provide an unexpectedly fast onset of therapeutic activity combined with substantially complete disintegration or dissolution of the formulation in less than about 3 minutes.

The rapidly disintegrating or dissolving solid dose formulations of nanoparticulate compositions comprise a poorly soluble nanoparticulate drug or other agent to be administered, having an effective average particle size of less than about 2000 nm, and a surface stabilizer adsorbed on the surface thereof. The nanoparticulate drug can be in a crystalline form, semi-crystalline form, amorphous form, or a combination thereof. In addition, the rapidly disintegrating or dissolving solid dose nanoparticulate compositions comprise at least one pharmaceutically acceptable water-soluble or water-dispersible excipient, which finctions to rapidly disintegrate or dissolve the solid dose matrix surrounding the nanoparticulate active agent upon contact with saliva, thereby presenting the nanoparticulate active agent for absorption.

Preferably, the effective average particle size of the nanoparticulate active agent in the composition is less than about 2000 nm, less than about 1500 nm, less than about 1000 nm, less than about 600 nm, less than about 400 nm, less than about 300 nm, less than about 250 mn, less than about 100 nm, or less than about 50 nm.

In another aspect of the invention there is provided a method of preparing rapidly disintegrating or dissolving nanoparticulate solid dose oral formulations. The method comprises: (1) forming a nanoparticulate composition comprising an active agent to be administered and a surface stabilizer; (2) adding at least one pharmaceutically acceptable water-soluble or water-dispersible excipient, and (3) forming a solid dose form of the composition for oral administration. Additional pharmaceutically acceptable excipients can also be added to the composition for administration. Methods of making nanoparticulate compositions, which can comprise mechanical grinding, precipitation, or any other suitable size reduction process, are known in the art and are described in, for example, the '684 patent.

Yet another aspect of the present invention provides a method of treating a mammal, including a human, requiring rapid onset of therapeutic activity with a rapidly disintegrating nanoparticulate composition of the invention.

It is to be understood that both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWING

FIG. 1: Shows the rate of dissolution over time for three rapidly disintegrating or dissolving nanoparticulate dosage forms of Compound A, which is a COX-2 inhibitor type nonsteroidal anti-inflammatory drug (NSAID), having anti-inflammatory, analgesic, and antipyretic activities.

FIG. 2: Shows an exemplary fluid bed granulation process.

DETAILED DESCRIPTION OF THE INVENTION

A. RAPIDLY DISINTEGRATING OR DISSOLVING NANOPARTICULATE COMPOSITIONS

This invention is directed to the surprising and unexpected discovery of new solid dose rapidly disintegrating or dissolving nanoparticulate compositions of poorly soluble drugs having fast onset of drug activity. The rapidly disintegrating or dissolving solid oral dosage form of the invention has the advantage of combining rapid presentation of the poorly soluble active agent as a result of the rapid disintegration, and rapid dissolution of the poorly soluble drug in the oral cavity as a result of the nanoparticulate size of the drug.

This combination of rapid disintegration and rapid dissolution reduces the delay in the onset of therapeutic action associated with prior known rapidly dissolving dosage forms of poorly soluble drugs. Further, the opportunity for buccal absorption of the poorly soluble active ingredient is enhanced with the present invention. Yet another advantage of nanoparticulate rapidly disintegrating or dissolving solid dose forms is that the use of nanoparticulate drug particles eliminates or minimizes the feeling of grittiness found with prior art fast melt formulations of poorly soluble drugs.

Rapidly disintegrating or dissolving dosage forms, also known as fast dissolve, fast or rapid melt, and quick disintegrating dosage forms, dissolve or disintegrate rapidly in the patient's mouth without chewing or the need for water within a short time frame. Because of their ease of administration, such compositions are particularly useful for the specific needs of pediatrics, geriatrics, and patients with dysphagia. Rapidly dissolving dosage forms can be beneficial because of their ease of administration, convenience, and patient-friendly nature. It is estimated that 35% to 50% of the population finds it difficult to swallow tablets and hard gelatin capsules, particularly pediatric and geriatric patients. Rapidly disintegrating or dissolving dosage forms eliminate the need to swallow a tablet or capsule. Moreover, rapidly disintegrating or dissolving dosage forms do not require the addition of water or chewing.

One advantage typically associated with fast melt dosage forms is a reduction of the time lag between administration of a dose and the physical presentation of the active ingredient. This lag time is usually associated with the break up of the dosage form and the distribution of the active ingredient thereafter. A second advantage of fast melt dosage forms is that the rapid presentation of the drug in the mouth upon administration may facilitate buccal absorption of the active ingredient directly into the blood stream, thus reducing the first pass effect of the liver on the overall bioavailability of active ingredient from a unit dose. This second advantage is dramatically enhanced for the fast melt formulations of the invention, as the nanoparticulate size of the active agent enables rapid dissolution in the oral cavity.

The solid dose rapidly disintegrating nanoparticulate formulations of the invention comprise a poorly soluble nanoparticulate active agent to be administered, having an effective average particle size prior to inclusion in the dosage form of less than about 2000 nm, at least one surface stabilizer adsorbed on the surface thereof, and at least one pharmaceutically acceptable water-soluble or water-dispersible excipient, which finctions to rapidly disintegrate the matrix of the solid dose form upon contact with saliva, thereby presenting the nanoparticulate active agent for absorption. The oorly soluble nanoparticulate active agent can be in a crystalline form, semi-crystalline form, amorphous form, or a combination thereof.

Preferably, the effective average particle size of the nanoparticulate active agent prior to inclusion in the dosage form is less than about 1500 nm, less than about 1000 nm, less than about 600 nm, less than about 400 nm, less than about 300 nm, less than about 250 nm, less than about 100 nm, or less than about 50 nm. Nanoparticulate compositions were first described in the '684 patent.

A rapidly disintegrating nanoparticulate solid oral dosage form according to the invention has a disintegration time of less than about 3 minutes upon addition to an aqueous medium. More preferably, the fast melt nanoparticulate solid oral dosage form has a disintegration or dissolution time upon addition to an aqueous medium of less than about 2 minutes, less than about 90 seconds, less than about 60 seconds, less than about 45 seconds, less than about 30 seconds, less than about 20 seconds, less than about 15 seconds, less than about 10 seconds, or less than about 5 seconds.

Surprisingly, the rapidly disintegrating or dissolving nanoparticulate dosage forms can have a relatively high degree of tensile strength. Tensile strength is determined by the hardness, size, and geometry of the solid dose. This is significant because if a solid does (i.e., a tablet) is too brittle it will crumble or fragment. Such brittle tablets can also be difficult and expensive to package. Thus, the ideal rapidly disintegrating solid oral dose should have a degree of tensile strength to allow ease of packaging while also rapidly disintegrating upon administration. The rapidly disintegrating or dissolving solid dose nanoparticulate compositions can be formulated to mask the unpleasant taste of an active agent. Such taste masking can be accomplished, for example, by the addition of one or more sweet tasting excipients, by coating the poorly soluble nanoparticulate active agent and stabilizer with a sweet tasting excipient, and/or by coating a dosage form of poorly soluble nanoparticulate active agent, stabilizer, and excipients with a sweet tasting excipient.

1. Nanoparticulate Compositions

The starting nanoparticulate composition (prior to formulation into a fast melt dosage form) comprises a poorly soluble active agent to be administered and at least one surface stabilizer adsorbed on the surface thereof.

a. Poorly Soluble Active Agent

The nanoparticles of the invention comprise a poorly soluble therapeutic agent, diagnostic agent, or other active agent to be administered for rapid onset of activity. A therapeutic agent can be a drug or pharmaceutical and a diagnostic agent is typically a contrast agent, such as an x-ray contrast agent, or any other type of diagnostic material.

The invention can be practiced with a wide variety of poorly soluble drugs or diagnostic agents. The drug or diagnostic agent is preferably present in an essentially pure form, is poorly water soluble, and is dispersible in at least one liquid medium. By "poorly water soluble" it is meant that the drug or diagnostic agent has a solubility in the liquid dispersion medium of less than about 30 mg/ml, preferably less than about 10 mg/ml, and more preferably less than about 1 mg/ml.

The poorly soluble active agent can be selected from a variety of known classes of drugs or diagnostic agents, including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of drugs and diagnostic agents and a listing of species within each class can be found in Martindale, The Extra Pharmacopoeia, Twenty-ninth Edition (The Pharmaceutical Press, London, 1989), specifically incorporated by reference. The drugs or diagnostic agents are commercially available and/or can be prepared by techniques known in the art.

The poorly soluble active ingredient may be present in any amount which is sufficient to elicit a therapeutic effect and, where applicable, may be present either substantially in the form of one optically pure enantiomer or as a mixture, racemic or otherwise, of enantiomers.

b. Surface Stabilizers

Usefull surface stabilizers, which are known in the art and described in the '684 patent, are believed to include those which physically adhere to the surface of the active agent but do not chemically bond to or interact with the active agent. The surface stabilizer is adsorbed on the surface of the active agent in an amount sufficient to maintain an effective average particle size of less than about 2000 nm for the active agent. Furthermore, the individually adsorbed molecules of the surface stabilizer are essentially free of intermolecular cross-linkages. Two or more surface stabilizers can be employed in the compositions and methods of the invention.

Suitable surface stabilizers can preferably be selected from known organic and inorganic pharmaceutical excipients. Such excipients include various polymers, low molecular weight oligomers, natural products, and surfactants. Preferred surface stabilizers include nonionic and ionic surfactants.

Representative examples of surface stabilizers include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-lOG® or Surfactant 10-G® (Olin Chemicals, Stamford, Conn.); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like.

Most of these surface stabilizers are known pharmaceutical excipients and are described in detail in the *Handbook of pharmaceutical Excipients*, published jointly by the American Pharmaceutical Association and The Pharmaceutical Society of Great Britain (The Pharmaceutical Press, 1986), specifically incorporated by reference.

c. Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifuigation.

By "an effective average particle size of less than about 2000 nm" it is meant that at least 50% of the active agent particles have an average particle size of less than about 2000 nm when measured by the above techniques. Preferably, at least 70% of the particles have an average particle size of less than the effective average, i.e., about 2000 nm, more preferably at least about 90% of the particles have an average particle size of less than the effective average. In preferred embodiments, the effective average particle size is less than about 1500 nm, less than about 1000 nm, less than about 600 nm, less than about 400 nm, less than about 300 nm, less than about 250 nm, less than about 100 nm, or less than about 50 nm.

2. Pharmaceutically Acceptable Water-Soluble or Water-Dispersible Excipient

The pharmaceutically acceptable water-soluble or water-dispersible excipient is typically a sugar, such as lactose, glucose, or mannose; a sugar alcohol, such as mannitol, sorbitol, xylitol, erythritol, lactitol, or maltitol; a starch or modified starch, such as corn starch, potato starch, or maize starch; a natural polymer or a synthetic derivative of a natural polymer, such as gelatin, carrageenin, an alginate, dextran, or maltodextran; a natural gum such as acacia or xanthan gum; a synthetic polymer, such as polyethylene glycol, polyvinylpyrrolidone, polyvinylalcohol, polyoxyethylene copolymers, polyoxypropylene copolymers, or polyethyleneoxide; or a mixture of any of these compounds. The pharmaceutically acceptable water-soluble or water-dispersible excipient can be a direct compression or a non-direct compression disintegrant.

3. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicifized microcrystalline cellulose (SMCC).

Suitable lubricants, including agents that act on the flowability of the powder to be compressed, are colloidal silicon dioxide, such as Aerosil® 200; talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102;lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-provide, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present.

4. Quantities of Nanoparticulate-Composition and Pharmaceutically Acceptable Water-Soluble or Water-Dispersible Excipient The relative amount of nanoparticulate composition in the rapidly disintegrating formulations of the invention can vary widely and can depend upon, for example, the compound selected for delivery, the melting point of the compound, the water solubility of the compound, the surface tension of water solutions of the compound, etc. The poorly soluble active agent or pharmaceutically acceptable salt thereof may be present in any amount which is sufficient to elicit a therapeutic effect and, where applicable, may be present either substantially in the form of one optically pure enantiomer or as a mixture, racemic or otherwise, of enantiomers.

The nanoparticulate active agent composition can be present in the rapidly disintegrating formulations of the invention in an amount of about 0.1% to about 99.9% (w/w), preferably about 5% to about 70% (w/w), and most preferably about 15% to about 40% (w/w), based on the total weight of the dry composition.

The one or more pharmaceutically acceptable water-soluble or water-dispersible excipients can be present in an amount of about 99.9% to about 0.1% (w/w), preferably about 95% to about 30% (w/w), and most preferably about 85% to about 60% (w/w), by weight based on the total weight of the dry composition.

B. METHODS OF MAKING RAPIDLY DISINTEGRATING SOLID DOSE NANOPARTICULATE COMPOSITIONS

In another aspect of the invention there is provided a method of preparing rapidly disintegrating or dissolving nanoparticulate solid dose oral formulations. The method comprises: (1) forming a nanoparticulate composition comprising an active agent to be administered and at least one surface stabilizer; (2) adding one or more pharmaceutically acceptable water-soluble or water-dispersible excipients, and (3) forming a solid dose form of the composition for administration. Pharmaceutically acceptable excipients can also be added to the composition for administration. Methods of making nanoparticulate compositions, which can comprise mechanical grinding, precipitation, or any other suitable size reduction process, are known in the art and are described in, for example, the '684 patent.

Methods of making solid dose pharmaceutical formulations are known in the art, and such methods can be employed in the present invention. Exemplary rapidly disintegrating or dissolving solid dose formulations of the invention can be prepared by, for example, combining the one or more pharmaceutically acceptable water-soluble or water-dispersible excipients with a raw nanoparticulate dispersion obtained after size reduction of an agent to be administered. The resultant composition can be formulated into tablets for oral administration. Alternatively, the nanoparticulate dispersion can be spray dried, followed by blending with one or more pharmaceutically acceptable water-soluble or water-dispersible excipients and tableting. The nanoparticulate dispersion and desired excipients can also be lyophilized to form a fast melt formulation, or the nanoparticulate dispersion can be granulated to form a powder, followed by tableting.

1. Spray Drying of Nanoparticulate Dispersions

Solid dose forms of nanoparticulate dispersions can be prepared by drying the nanoparticulate formulation following size reduction. A preferred drying method is spray drying. The spray drying process is used to obtain a nanoparticulate powder following the size reduction process used to transform the active agent into nanoparticulate sized particles. Such a nanoparticulate powder can be formulated into tablets for oral administration.

In an exemplary spray drying process, the nanoparticulate active agent suspension is fed to an atomizer using a peristaltic pump and atomized into a fine spray of droplets. The spray is contacted with hot air in the drying chamber resulting in the evaporation of moisture from the droplets. The resulting spray is passed into a cyclone where the powder is separated and collected. The nanoparticulate dispersion can be spray-dried in the presence or absence of excipients to give the spray-dried intermediate powder.

2. Lyophilization

A rapidly disintegrating solid oral dosage form of the invention can be prepared by lyophilizing a nanoparticulate dispersion of the poorly soluble active agent and stabilizer. Suitable lyophilization conditions include, for example, those described in EP 0,363,365 (McNeil-PPC Inc.), U.S. Pat. No. 4,178,695 (A. Erbeia), and U.S. Pat. No. 5,384,124 (Farmalyoc), all of which are incorporated herein by reference. Typically, the nanoparticulate dispersion is placed in a suitable vessel and frozen to a temperature of between about −5° C. to about −100° C. The frozen dispersion is then subjected to reduced pressure for a period of up to about 48 hours. The combination of parameters such as temperature, pressure, dispersion medium, and batch size will impact the time required for the lyophilization process. Under conditions of reduced temperature and pressure, the frozen solvent is removed by sublimation yielding a solid, porous, rapidly disintegrating solid oral dosage form having the active ingredient distributed throughout.

3. Granulation

Alternatively, a rapidly disintegrating solid oral dosage form of the invention can be prepared by granulating in a fluidized bed an admixture comprising a nanoparticulate dispersion of active agent and at least one surface stabilizer with a solution of at least one pharmaceutically acceptable water-soluble or water-dispersible excipient, to form a granulate. This is followed by tableting of the granulate to form a solid oral dosage form.

4. Tableting

The rapidly disintegrating nanoparticulate solid formulations of the invention can be in the form of tablets for oral administration. Preparation of such tablets can be by pharmaceutical compression or molding techniques known in the art. The tablets of the invention may take any appropriate shape, such as discoid, round, oval, oblong, cylindrical, triangular, hexagonal, and the like.

Powders for tableting can be formulated into tablets by any method known in the art. Suitable methods include, but are not limited to, milling, fluid bed granulation, dry granulation, direct compression, spheronization, spray congealing, and spray-dying. Detailed descriptions of tableting methods are provided in Remington: *The Science and Practice of Pharmacy*, 19th ed. Vol. 11 (1995) (Mack Publishing Co., Pennsylvania); and *Remington's Pharmaceutical Sciences*, Chapter 89, pp. 1633–1658 (Mach Publishing Company, 1990), both of which are specifically incorporated by reference.

In an exemplary process, a rapidly disintegrating dosage form can be prepared by blending a nanoparticulate composition, comprising a poorly soluble active agent and at least one surface stabilizer, with at least one pharmaceutically acceptable water-soluble or water-dispersible excipient, and, optionally, other excipients to form a blend which is then directly compressed into tablets. For example, spray-dried nanoparticulate powder can be blended with tablet excipients using a V-blender® (Blend Master Lab Blender, Patterson Kelley Co.) or high-shear mixer, followed by compression of the powder using, for example, an automated Carver press (Carver Laboratory Equipment), single station Korsch® press, or a high-speed Fette® tablet press.

The tablets may be coated or uncoated. If coated they may be sugar-coated (to cover objectionable tastes or odors and to protect against oxidation) or film coated (a thin film of water soluble matter for similar purposes).

C. ADMINISTRATION OF RAPIDLY DISINTEGRATING OR DISSOLVING SOLID DOSE NANOPARTICULATE COMPOSITIONS

The present invention provides a method of treating a mammal, including a human, requiring the rapid availability of a poorly soluble active ingredient. The administered rapidly disintegrating or dissolving nanoparticulate compositions of the invention rapidly release an incorporated active agent resulting in fast onset of activity.

In general, the compositions of the invention will be administered orally to a mammalian subject in need thereof using a level of drug or active agent that is sufficient to provide the desired physiological effect. The mammalian subject may be a domestic animal or pet but preferably is a human subject. The level of drug or active agent needed to give the desired physiological result is readily determined by one of ordinary skill in the art by referring to standard texts, such as Goodman and Gillman and the Physician's Desk Reference.

The following examples are given to illustrate the present invention. It should be understood, however, that the invention is not to be limited to the specific conditions or details described in these examples. Throughout the specification, any and all references to a publicly available documents are specifically incorporated into this patent application by reference.

EXAMPLE 1

The purpose of this example was to prepare a rapidly disintegrating nanoparticulate dosage form of Compound A using a fluid bed granulation process. Compound A is a COX-2 inhibitor type nonsteroidal anti-inflammatory drug (NSAID), having anti-inflammatory, analgesic, and antipyretic activities.

The fluid bed granulation process comprises fluidizing a binder dispersion and/or solution and spraying the resultant composition over a Fluidized power bed to form granules. It is also possible to dry and coat pharmaceuticals using a fluid bed granulator.

An exemplary fluid bed granulation process is shown FIG. 2.

A dispersion of Compound A, having 20% drug, 4% hydroxypropyl cellulose SL (HPC-SL), and 0.12% sodium lauryl sulfate (SLS), was used for the fluid bed granulation process. 100 g of the dispersion was sprayed on 125.0 g of fluidized lactose powder in a fluidized bed granulator (Aeromatic Fielder, Inc., Model STREA-1). Compound A had a mean particle size of 120 nm.

The instrument settings for the fluid bed granulator were as follows:

| | |
|---|---|
| Inlet Temperature | 49–52° C. |
| Outlet Temperature: | 25–34° C. |
| Atomizing Pressure: | 1.5 bar |
| Blow Out Pressure: | 3–4 bar |
| Blow Back Dwell Setting | 2 bar |
| Capacity of Fan | 1–9 |

After spraying the dispersion on the fluidized lactose to form granules of nanoparticulate Compound A (comprising Compound A, HPC-SL, and SLS) and lactose, the tubings of the granulator were washed with approximately 10 g of deionized water. The washings were also sprayed on the granules of nanoparticulate Compound A and lactose.

The granules were dried for approximately 10 min, followed by sieving through a #16 mesh screen. The sieved granules were used for preparing rapidly disintegrating tablets having the composition shown in Table 1.

TABLE 1

Fast Melt Compound A Tablets

| Ingredient | Composition Per Tablet (mg) | Batch Formula (20 Tablets) (g) |
|---|---|---|
| Fluidized Bed Granules of lactose and nanoparticulate Compound A (Compound A, HPC-SL, and SLS) | 746.0 | 14.92 |
| fructose | 731 | 14.620 |
| sorbitol | 243 | 4.860 |

TABLE 1-continued

Fast Melt Compound A Tablets

| Ingredient | Composition Per Tablet (mg) | Batch Formula (20 Tablets) (g) |
| --- | --- | --- |
| croscarmellose sodium (Ac-di-sol ®; FMC Corp.) | 160 | 3.20 |
| citric acid | 100 | 2.0 |
| Magnesium stearate | 20 | 0.4 |
| Total | 2000 | 20.0 |

The fluidized bed granules of nanoparticulate Compound A (Compound A, HPC-SL, and SLS) and lactose were blended with all of the excipients except magnesium stearate in a V-blender for about 20 minutes, followed by the addition of magnesium stearate and blending for 2 minutes. The powder blend was compressed to form tablets using a Carver press using 1 inch tooling under the conditions given in Table 2.

TABLE 2

Compression Force of Fast Melt Compound A Tablets

| Tablet | Compression Force (lbs) |
| --- | --- |
| Tablet A | 1800 |
| Tablet B | 2800 |
| Tablet C | 3800 |

EXAMPLE 2

The purpose of this example was to test the disintegration, hardness, and dissolution of the Compound A tablets prepared in Example 1.

Tablets A, B, and C were first evaluated for hardness and disintegration. An average of two tablets for each formulation were used for the data. Tablets A and B had a hardness of less than 1 kP and Tablet C had a hardness of 1.7 kP.

For the disintegration determination, a Haake disintegration tester containing 710 micron sieves were used to test Tablet A, B, and C in a 1000 ml deionized water bath at 37° C. Disintegration and dissolution measurements were performed in accordance with USP 20. The disintegration results are shown below in Table 3.

TABLE 3

Disintegration Times for Fast Melt Compound A Tablets

| Tablet | Time Required for Complete Disintegration (seconds) |
| --- | --- |
| Tablet A | 112 |
| Tablet B | 108 |
| Tablet C | 111 |

All of the Compound A tablets completely disintegrated in less than 2 minutes, demonstrating the rapid disintegration characteristic of the nanoparticulate dosage form.

Tablets A, B, and C (100 mg each) were evaluated for dissolution in a 1% solution of SLS at 37° C. in a Distek dissolution system. The rotation speed of the paddle of the Distek dissolution system was 50 rpm. The results, given in FIG. 1, show that all of the tablets had at least about 80% dissolution after 10 minutes, with complete dissolution at from 15 to 20 minutes.

EXAMPLE 3

The purpose of this example was to prepare a rapidly disintegrating nanoparticulate dosage form of ketoprofen using a fluid bed granulation process. Ketoprofen is an nonsteroidal anti-inflammatory drug used to treat mild to moderate pain resulting from arthritis, sunburn treatment, menstrual pain, and fever.

A nanoparticulate dispersion of ketoprofen was prepared, having 30% drug, 3% polyvinylpyrrolidone (PVP), and 0.15% sodium lauryl sulfate (SLS). The ketoprofen had a mean particle size of about 151 nm. 200.0 g of the nanoparticulate dispersion of ketoprofen was sprayed using a Masterflex pump (Cole-Parmer Instrument Co., Chicago, Ill.) on 150.0 g of fluidized spray-dried mannitol powder (Pearlitol® SD200, Roquette, Inc.) in a fluidized bed granulator (Aeromatic Fielder, Inc., Model STREA-1). Spray-dried mannitol powder is a direct compression grade powder. Pearlitol® is spray-dried mannitol, which is a free-flowing, direct compression material.

The instrument settings for the fluid bed granulator were as follows:

| Inlet Temperature | 49–52° C. |
| --- | --- |
| Outlet Temperature: | 25–34° C. |
| Atomizing Pressure: | 1.5 bar |
| Blow-Out Pressure: | 4–6 bar |
| Blow-Back Dwell Setting | 2 bar |
| Capacity of Fan | 1–9 |

After spraying the ketoprofen nanoparticulate dispersion on the fluidized mannitol to form granules, approximately 20 g of deionized water was passed through the feed tubing and sprayed on the granules. At the end of the spraying process the granules were dried by fluidizing for 5–7 minutes. Finally, the granules were harvested, passed through a #35 sieve, and weighed, for a yield of 186.7 g.

The fluidized bed granules of nanoparticulate ketoprofen were combined with magnesium stearate in a V-blender as shown below for about 2 minutes to form a powder blend.

TABLE 4

Fast Melt Ketoprofen Tablets

| Ingredient | Composition Per Tablet (mg) | Batch Formula (20 Tablets) (g) |
| --- | --- | --- |
| Fluidized Bed Granules of Nanoparticulate ketoprofen (ketoprofen, PVP, and SLS) and spray-dried mannitol | 400 | 12.0 |
| magnesium stearate | 2 | 0.06 |
| Total | 402 | 12.06 |

The powder blend was compressed to form tablets using a Carver press using ⅝ inch Troche tooling under the conditions shown in Table 5. Troche tooling refers to a tablet having a slightly indented center.

TABLE 5

Compression Force of Fast Melt Ketoprofen Tablets

| Tablet | Compression Force (lbs) |
|---|---|
| Tablet D | 700 |
| Tablet E | 1200 |
| Tablet F | 1500 |

EXAMPLE 4

The purpose of this example was to prepare a rapidly disintegrating nanoparticulate dosage form of ketoprofen using fluidized bed granules of nanoparticulate ketoprofen.

The fluidized bed granules of nanoparticulate ketoprofen prepared in Example 3 were used in this example. The fluidized bed granules of nanoparticulate ketoprofen were combined with spray-dried mannitol powder (Pearlitol® SD200, Roquette, Inc.) and blended in a V-blender for about 20 minutes, followed by the addition of magnesium stearate and blending for 2 minutes to form a powder blend, in the amounts shown below in Table 6.

TABLE 6

Fast Melt Ketoprofen Tablets

| Ingredient | Composition Per Tablet (mg) | Batch Formula (20 Tablets) (g) |
|---|---|---|
| Fluidized Bed Granules of Nanoparticulate ketoprofen (ketoprofen, PVP, and SLS) and spray-dried mannitol (Pearlitol ®) | 400 | 8.0 |
| spray-dried mannitol (Pearlitol ®) | 197 | 3.94 |
| magnesium stearate | 3 | 0.06 |
| Total | 600 | 12.0 |

The powder blend was compressed to form tablets using a Carver press having ⅝ inch Troche tooling under the conditions shown in Table 7.

TABLE 7

Compression Force of Fast Melt Ketoprofen Tablets

| Tablet | Compression Force (lbs) |
|---|---|
| Tablet G | 1800 |
| Tablet H | 2800 |
| Tablet I | 3800 |

EXAMPLE 5

The purpose of this example was to prepare a rapidly disintegrating nanoparticulate dosage form of ketoprofen using fluidized bed granules of nanoparticulate ketoprofen.

The fluidized bed granules of nanoparticulate ketoprofen prepared in Example 3 were used in this example. The fluidized bed granules of nanoparticulate ketoprofen were combined with spray-dried mannitol powder (Pearlitol® SD200, Roquette, Inc.) and croscarmellose sodium (Ac-di-sol®) and blended in a V-blender for about 20 minutes, followed by the addition of magnesium stearate and blending for 2 minutes to 20 form a powder blend, in the amounts shown in Table 8.

TABLE 8

Fast Melt Ketoprofen Tablets

| Ingredient | Composition Per Tablet (mg) | Batch Formula (20 Tablets) (g) |
|---|---|---|
| Fluidized Bed Granules of Nanoparticulate ketoprofen (ketoprofen, PVP, and SLS) and spray-dried mannitol (Pearlitol ®) | 400 | 8.0 |
| spray-dried mannitol (Pearlitol ®) | 179 | 3.58 |
| croscarmellose sodium (Ac-di-sol ®) | 18 | 0.36 |
| magnesium stearate | 3 | 0.06 |
| Total | 600 | 12.0 |

The powder blend was compressed to form tablets using a Carver press using ⅝ inch tooling under the conditions shown in Table 9.

TABLE 9

Compression Force of Fast Melt Ketoprofen Tablets

| Tablet | Compression Force (lbs) |
|---|---|
| Tablet J | 800 |
| Tablet K | 1000 |
| Tablet L | 1300 |

EXAMPLE 6

The purpose of this example was to test the hardness and disintegration of the ketoprofen tablets prepared in Examples 3, 4, and 5.

Tablets D–L were first evaluated for their hardness. Two tablets of each sample were tested. The results of the hardness testing are given in Table 10.

TABLE 10

Hardness of Fast Melt Ketoprofen Tablets Prepared in Examples 3, 4, and 5

| Tablet | Hardness of Sample 1 (kP) | Hardness of Sample 2 (kP) |
|---|---|---|
| Tablet D | 2.7 | 2.9 |
| Tablet E | 4.0 | 4.3 |
| Tablet F | 5.2 | 4.9 |
| Tablet G | 3.0 | 2.8 |
| Tablet H | 4.3 | 4.2 |
| Tablet I | 6.1 | 6.3 |
| Tablet J | 2.2 | 2.1 |
| Tablet K | 4.1 | 3.9 |
| Tablet L | 5.2 | 5.5 |

For the disintegration determination, a Haake disintegration tester (Haake, Germany) was used to test the rate of dissolution of Tablets D–L in a 1000 ml deionized water bath at 37° C. For tablets made using Troche tooling (having an indented center), complete disintegration and dissolution was determined to be when all of the tablet surrounding the small core had disintegrated and dissolved. The disintegration results are shown below in Table 11.

TABLE 11

Disintegration Times of Fast Melt Ketoprofen
Tablets Prepared in Examples 3, 4, and 5

| Tablet | Time Required for Complete Disintegration of Sample 1 (seconds) | Time Required for Complete Disintegration of Sample 2 (seconds) |
|---|---|---|
| Tablet D | 219 | 260 |
| Tablet E | 404 | 448 |
| Tablet F | 749 | 770 |
| Tablet G | 230 | 231 |
| Tablet H | 262 | 276 |
| Tablet I | 333 | 345 |
| Tablet J | 60 | 74 |
| Tablet K | 70 | 76 |
| Tablet L | 69 | 78 |

Tablets J, K, and L, having additional spray-dried mannitol blended with the fluidized bed ketoprofen granules, showed the most rapid disintegration, with complete disintegration obtained after slightly more than 1 minute, demonstrating the rapid disintegration characteristic of the nanoparticulate dosage form.

EXAMPLE 7

The purpose of this example was to prepare a rapidly disintegrating nanoparticulate dosage form of ketoprofen using fluidized bed granules of nanoparticulate ketoprofen.

The fluidized bed granules of nanoparticulate ketoprofen prepared in Example 3 were used in this example. The fluidized bed granules of nanoparticulate ketoprofen were combined with spray-dried mannitol powder (Pearlitol® SD200, Roquette, Inc.) and croscarmellose sodium (Ac-di-sol®) and blended in a V-blender for about 20 minutes, followed by the addition of magnesium stearate and blending for 2 minutes to form a powder blend, in the amounts shown below in Table 12.

TABLE 12

Fast Melt Ketoprofen Tablets

| Ingredient | Composition Per Tablet (mg) | Batch Formula (20 Tablets) (g) |
|---|---|---|
| Fluidized Bed Granules of spray-dried mannitol (Pearlitol ® SD200) and nanoparticulate ketoprofen (ketoprofen, PVP, and SLS) | 400 | 8.0 |
| spray-dried mannitol (Pearlitol ® SD200) | 167 | 3.34 |
| croscarmellose sodium (Ac-di-sol ®) | 30 | 0.6 |
| magnesium stearate | 3 | 0.06 |
| Total | 600 | 12.0 |

The powder blend was compressed to form tablets using a Carver press using ⅝ inch Troche tooling under the conditions shown in Table 13.

TABLE 13

Compression Force of Fast Melt Ketoprofen Tablets

| Tablet | Compression Force (lbs) |
|---|---|
| Tablet M | 800 |
| Tablet N | 1000 |
| Tablet O | 1300 |

EXAMPLE 8

The purpose of this example was to prepare a rapidly disintegrating nanoparticulate dosage form of ketoprofen using fluidized bed granules of nanoparticulate ketoprofen.

The fluidized bed granules of nanoparticulate ketoprofen prepared in Example 3 were used in this example. The fluidized bed granules of nanoparticulate ketoprofen were combined with spray-dried mannitol powder (Pearlitol® SD200, Roquette, Inc.) and croscarmellose sodium (Ac-di-sol®) and blended in a V-blender for about 20 minutes, followed by the addition of magnesium stearate and blending for 2 minutes to form a powder blend, in the amounts shown below in Table 14.

TABLE 14

Fast Melt Ketoprofen Tablets

| Ingredient | Composition Per Tablet (mg) | Batch Formula (20 Tablets) (g) |
|---|---|---|
| Fluidized Bed Granules of spray-dried mannitol (Pearlitol ® SD200) and nanoparticulate ketoprofen (ketoprofen, PVP, and SLS) | 400 | 8.0 |
| spray-dried mannitol (Pearlitol ® SD200) | 155 | 3.1 |
| croscarmellose sodium (Ac-di-sol ®) | 42 | 0.84 |
| magnesium stearate | 3 | 0.06 |
| Total | 600 | 12.0 |

The powder blend was compressed to form tablets using a Carver press and ⅜ inch Troche tooling under the conditions shown in Table 15.

TABLE 15

Compression Force of Fast Melt Ketoprofen Tablets

| Tablet | Compression Force (lbs) |
|---|---|
| Tablet P | 800 |
| Tablet Q | 1000 |
| Tablet R | 1300 |

EXAMPLE 9

The purpose of this example was to test the hardness and disintegration of the ketoprofen tablets prepared in Examples 7 and 8.

Tablets M–R were first evaluated for their hardness. Two tablets of each formulation were tested. The results are shown below in Table 16.

TABLE 16

Hardness of Fast Melt Ketoprofen Tablets Prepared in Examples 7 and 8

| Tablet | Hardness of Sample 1 (kP) | Hardness of Sample 2 (kP) |
|---|---|---|
| Tablet M | 1.9 | 1.7 |
| Tablet N | 3.5 | 3.0 |
| Tablet O | 5.3 | 5.4 |
| Tablet P | 1.7 | 1.3 |
| Tablet Q | 3.0 | 2.7 |
| Tablet R | 5.2 | 4.7 |

For the disintegration determination, a Haake disintegration tester was used to test the rate of dissolution of Tablets M–R in a 1000 ml deionized water bath at 37° C. The disintegration results are shown below in Table 17.

TABLE 17

Disintegration Times of Fast Melt Ketoprofen Tablets Prepared in Examples 7 and 8

| Tablet | Time Required for Complete Disintegration of Sample 1 (seconds) | Time Required for Complete Disintegration of Sample 2 (seconds) |
|---|---|---|
| Tablet M | 66 | 71 |
| Tablet N | 78 | 87 |
| Tablet O | 70 | 81 |
| Tablet P | 67 | 72 |
| Tablet Q | 78 | 89 |
| Tablet R | 76 | 83 |

All of the tablets showed complete disintegration in less than 90 seconds, demonstrating the rapid disintegration characteristic of the nanoparticulate dosage form.

EXAMPLE 10

The purpose of this example was to prepare a rapidly disintegrating nanoparticulate dosage form of ketoprofen using fluidized bed granules of nanoparticulate ketoprofen.

The fluidized bed granules of nanoparticulate ketoprofen prepared in Example 3 were used in this example. The fluidized bed granules of nanoparticulate ketoprofen were combined with spray-dried mannitol powder (Pearlitol® SD200, Roquette, Inc.), Aspartame®, anhydrous citric acid, orange type natural flavor, and croscarmellose sodium (Ac-di-sol®) and blended in a V-blender for about 20 minutes, followed by the addition of magnesium stearate and blending for 2 minutes to form a powder blend, in the amounts shown below.

TABLE 18

Fast Melt Ketoprofen Tablets

| Ingredient | Composition Per Tablet (mg) | Batch Formula (20 Tablets) (g) |
|---|---|---|
| Fluidized Bed Granules of nanoparticulate ketoprofen (ketoprofen, PVP, and SLS) and spray-dried mannitol (Pearlitol® SD200) | 185 | 3.7 |
| Aspartame® | 21.5 | 0.43 |
| citric acid (anhydrous) | 22.0 | 0.44 |
| orange type natural flavor SD | 5 | 0.1 |
| croscarmellose sodium (Ac-di-sol®) | 15 | 0.3 |
| magnesium stearate | 1.5 | 0.03 |
| Total | 250 | 5.0 |

The powder blend was compressed to form tablets using a Carver press under the conditions shown in Table 19.

TABLE 19

Tableting Conditions of the Fast Melt Ketoprofen Tablets

| Tablet | Compression Force (lbs) | Carver Press Tooling |
|---|---|---|
| Tablet S | 800 | ⅝ inch, Troch tooling |
| Tablet T | 100 | ⅝ inch, Troch tooling |
| Tablet U | 1300 | ⅝ inch, Troch tooling |
| Tablet V | 800 | ⅜ inch, flat-faced/biveled edge tooling |
| Tablet W | 1000 | ⅜ inch, flat-faced/biveled edge tooling |
| Tablet X | 1300 | ⅜ inch, flat-faced/biveled edge tooling |
| Tablet Y | 800 | ⅜ inch, Troch tooling |
| Tablet Z | 1000 | ⅜ inch, Troch tooling |
| Tablet AA | 1300 | ⅜ inch, Troch tooling |

EXAMPLE 11

The purpose of this example was to test the hardness and disintegration of the ketoprofen tablets prepared in Example 10.

Tablets S–AA were first evaluated for their hardness. One tablet was evaluated for each formulation. The hardness results are shown below in Table 20.

TABLE 20

Hardness Results of Fast Melt Ketoprofen Tablets Prepared in Example 10

| Tablet | Hardness of Sample (kP) |
|---|---|
| Tablet S | <1 |
| Tablet T | <1 |
| Tablet U | 1.2 |
| Tablet V | 2.9 |
| Tablet W | 3.4 |
| Tablet X | 5.0 |
| Tablet Y | 2.1 |
| Tablet Z | 3.2 |
| Tablet AA | 4.6 |

For the disintegration determination, a Haake disintegration tester was used to test the rate of dissolution of Tablets S–AA in a 1000 ml deionized water bath at 37° C. The disintegration results are shown below in Table 21.

TABLE 21

Disintegration Times for Fast Melt
Ketoprofen Tablets Prepared in Example 10

| Tablet | Time Required for Complete Disintegration of Tablets (seconds) |
|---|---|
| Tablet S | 8 |
| Tablet T | 12 |
| Tablet U | 18 |
| Tablet V | 40 |
| Tablet W | 90 |
| Tablet X | 211 |
| Tablet Y | 29 |
| Tablet Z | 78 |
| Tablet AA | 201 |

All of the tablets showed rapid disintegration, with 7 out of the 9 formulations showing disintegration in less than 90 seconds. Moreover, Tablets S–V and Y exhibited complete disintegration in less than 60 seconds, demonstrating the rapid disintegration characteristic of the nanoparticulate dosage form.

EXAMPLE 12

The purpose of this example was to prepare a rapidly disintegrating nanoparticulate dosage form of naproxen using fluidized bed granules of nanoparticulate naproxen and spray-dried lactose (Fast Flo® lactose, Foremost Whey Products, Baraboo, Wis. 53913) as an excipient. Spray-dried lactose powder is a direct compression (DC) grade powder. Naproxen is a well-known anti-inflammatory, analgesic, and antipyretic agent.

138.9 g of a naproxen nanoparticulate crystalline dispersion (28.5% naproxen (w/w) and 5/7% HPC (w/w)) was sprayed on 150.0 g of spray-dried lactose (Fast Flo® lactose) in a fluid bed granulator (Aeromatic Fielder, Inc., Model STREA-1). This was followed by sieving of the resultant granules through a 40# mesh screen to obtain the fluid bed granules (FBG).

The FBG were used to prepare two fast-melt tablet formulations, as shown in Table 22. The tablets were prepared using a ⅝ inch Troche tooling and a compression force of 1300 lbs.

TABLE 22

Fast Melt Naproxen Tablets

| Ingredient | Tablet A (mg) | Tablet B (mg) |
|---|---|---|
| Fluid Bed Granules of spray-dried lactose (Fast Flo ® lactose) and nanoparticulate naproxen (naproxen and HPC) | 400 | 400 |
| Spray Dried Lactose (Fast Flo ® lactose) | 179 | 0 |
| Spray Dried Mannitol (Pearlitol ® SD200) | 0 | 179 |
| croscarmellose sodium (Ac-di-sol ®) | 18 | 18 |
| Magnesium stearate | 3 | 3 |
| TOTAL | 600 | 600 |

Tablets of each formulation were analyzed for hardness and disintegration (Haake disintegration tester) as before. An average of two readings for each study was determined, with the results shown in Table 23.

TABLE 23

Hardness and Disintegration Times
of the Fast Melt Naproxen tablets

| Formulation | Hardness (kP) | Disintegration (sec) |
|---|---|---|
| Tablet A | 1.2 | 54 |
| Tablet B | 1.5 | 33 |

EXAMPLE 13

The purpose of this example was to prepare a fast melt formulation of nanoparticulate nifedipine. Nifedipine is a calcium channel blocker used to treat angina pectoris and high blood pressure. It is marketed under the trade names Procardia® (Pfizer, Inc.), Adalat® (Latoxan), and others.

A colloidal dispersion of nifedipine in water was prepared having 10% (w/w) nifedipine, 2% (w/w) hydroxypropyl cellulose (HPC), and 0.1% (w/w) sodium lauryl sulphate (SLS). Particle size analysis performed using a Malvern Mastersizer S2.14 (Malvern Instruments Ltd., Malvern, Worcestershire, UK) showed the following particle size characteristics: $D_{v,10}$=160 nm; $D_{v,50}$=290 nm; and $D_{v,90}$=510 nm.

The nanoparticulate nifedipine dispersion was prepared for spray drying by diluting 1:1 with purified water followed by homogenisation, and the addition of 10% (w/w) mannitol followed by homogenisation. The mixture obtained was spray-dried using a Buchi Mini B-191 spray drier system (Buchi, Switzerland).

Table 24 below shows a 10 mg nifidipine tablet formulation made by copession of the spray-dried nanoparticulate nifidipine powder.

TABLE 24

Fast Melt Nifedipine 10 mg Tablet Formulation

| Material | % |
|---|---|
| Spray dried nifedipine | 10.71 |
| Mannitol | 12.59 |
| Xylitol | 38.04 |
| Citric acid | 18.39 |
| Sodium bicarbonate | 18.21 |
| Aspartame ® | 0.27 |
| PEG 4000 | 0.89 |
| Sodium stearyl fumerate | 0.90 |

The fast melt 10 mg nifidipine tablet was prepared by first blending the ingredients given in the above table. The mannitol, xylitol, Aspartame®, half of the citric acid, and half of the sodium bicarbonate were mixed in a Uni-glatt (Glatt GmbH, Dresden, Germany). A 10% solution of PEG 4000 (polyethylene glycol having a molecular weight of about 4000) was used to granulate the mix at a spray rate of 10 g/min. The resultant granulate was dried for 30 minutes at about 40° C. after which the remainder of the citric acid and sodium bicarbonate, the spray-dried nifedipine nanocrystals, and the sodium stearyl fumarate were added and mixed.

The resultant blend was tableted to form nifedipine 10 mg tablets using a Piccalo RTS tablet press with 10.0 mm normal concave round tooling (Piccola Industria, Argentina). The tablets produced had a mean tablet weight of 304.2±3.9 mg and a means hardness of 53.55±6.85 N.

Disintegration testing was carried out on five representative tablets from each batch of tables pressed. Disintegration testing was carried out in purified water using a VanKel disintegration apparatus (VanKel, Edison, N.J.) at 32 oscillations per min. Results from the disintegration tests are given in Table 25 below.

TABLE 25

Disintegration Times for Fast-melt Nifedipine Tablets

| Batch No. | Disintegration time (sec) | | | | |
|---|---|---|---|---|---|
| | Tablet 1 | Tablet 2 | Tablet 3* | Tablet 4 | Tablet 5 |
| 1 | 54 | 55 | 42 | 55 | 59 |
| 2 | 54 | 62 | 46 | 56 | 60 |
| 3 | 54 | 62 | 49 | 57 | 60 |
| 4 | 55 | 63 | 50 | 59 | 60 |
| 5 | 55 | 63 | 50 | 65 | 60 |

(*All tests were carried out at 37° C. except Tablet 3 tests, which were carried out at 38° C.)

EXAMPLE 14

The purpose of this example was to prepare a fast melt formulation of nanoparticulate glipizide. Glipizide is a sulfonylurea drug used to lower blood sugar levels in people with non-insulin-dependent (type II) diabetes. It is marketed in the U.S. under the brand name Glucotrol® (Pratt Pharmaceuticals, Inc.).

A colloidal dispersion of glipizide in water was prepared having 10% (w/w) glipizide and 2% (w/w) hydroxypropyl cellulose (HPC). Particle size analysis performed using a Malvern Mastersizer S2.14 (Malvern Instruments Ltd., Malvern, Worcestershire, UK) recorded by a wet method showed the following particle size characteristics: $D_{v,10}$=270 nm; $D_{v,50}$=400 nm; and $D_{v,90}$=660 nm.

The nanoparticulate glipizide dispersion was prepared for spray drying by diluting 1:1 with purified water followed by homogenisation. Mannitol (10% (w/w)) was then added followed by homogenisation. The mixture obtained was spray-dried using a Buchi Mini B-191 spray drier system (Buchi, Switzerland).

A blend was prepared according to the formulation detailed in Table 26.

TABLE 26

Fast Melt Glipizide Tablets

| Material | % |
|---|---|
| Spray dried glipizide | 5.33 |
| Mannitol | 13.47 |
| Xylitol | 40.53 |
| Citric acid | 19.60 |
| Sodium bicarbonate | 19.33 |
| Aspartame ® | 0.28 |
| PEG 4000 | 0.93 |
| Sodium stearyl fumerate | 0.53 |

The mannitol, xylitol, Aspartame®, half of the citric acid, and half of the sodium bicarbonate were mixed in a Uni-glatt (Glatt GmbH, Dresden, Germany). A 10% solution of PEG 4000 was used to granulate the mix at a spray rate of 10 g/min. The resultant granulate was dried for 30 minutes at about 40° C., after which the remainder of the citric acid and sodium bicarbonate, the spray-dried glipizide nanocrystals, and the sodium stearyl fumerate were added and mixed.

The resultant blend was tableted to form glipizide 5 mg tablets using a Piccalo RTS tablet press with 10.0 mm normal concave round tooling (Piccola Industria, Argentina). The tablets produced had a mean tablet weight of 287.91±11.14 mg and a mean hardness of 39.4±8 N. Disintegration testing was carried out on representative tablets and as described above in Example 14 at 37 ° C. The average tablet disintegration time was found to be 43 seconds.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. An oral solid dose rapidly disintegrating nanoparticulate formulation comprising:
   (a) a solid dose matrix comprising at least one pharmaceutically acceptable water-soluble or water-dispersible excipient, and
   (b) within the solid dose matrix a nanoparticulate active agent composition comprising:
      (i) a poorly soluble active agent having an effective average particle size of less than about 2000 nm prior to inclusion in the dosage form; and
      (ii) at least one surface stabilizer adsorbed on the surface of the active agent;
   wherein the solid dose matrix surrounding the nanoparticulate active agent and at least one surface stabilizer substantially completely disintegrates or dissolves upon contact with saliva is less than about 3 minutes.

2. The composition of claim 1, wherein the effective average particle size of the active agent particles is less than about 1500 nm.

3. The composition of claim 1, wherein the solid dose matrix substantially completely disintegrates or dissolves upon contact with saliva in a time period selected from the group consisting of less than about 2 minutes, less than about 90 seconds, less than about 60 seconds, less than about 45 seconds, less than about 30 seconds, less than about 20 seconds, less than about 15 seconds, less than about 10 seconds, and less than about 5 seconds.

4. The composition of claim 1, wherein the concentration of the active agent is from about 0.1% to about 99.9% (w/w).

5. The composition of claim 4, wherein the concentration of the active agent is from about 5% to about 70% (w/w).

6. The composition of claim 5, wherein the concentration of the active agent is from about 15% to about 40% (w/w).

7. The composition of claim 1, wherein the concentration of the pharmaceutically acceptable water-soluble or water-dispersible excipient is from about 99.9% to about 0.1% (w/w).

8. The composition of claim 7, wherein the concentration of the pharmaceutically acceptable water-soluble or water-dispersible excipient is from about 95% to about 30% (w/w).

9. The composition of claim 8, wherein the concentration of the pharmaceutically acceptable water-soluble or water-dispersible excipient is from about 85% to about 60% (w/w).

10. The composition of claim 1, wherein said at least one pharmaceutically acceptable water-soluble or water-dispersible excipient is selected from the group consisting of a sugar, a sugar alcohol, a starch, a natural gum, a natural polymer, a synthetic derivative of a natural polymer, a synthetic polymer, and mixtures thereof.

11. The composition of claim 10, wherein said at least one pharmaceutically acceptable water-soluble or water-dispersible excipient is selected from the group consisting of lactose, glucose, mannose, mannitol, sorbitol, xylitol, erythritol, lactitol, maltitol, corn starch, potato starch, maize starch, gelatin, carrageenin, acacia, xanthan gum, an alginate, dextran, maltodextran, polyethylene glycol, polyvinylpyrrolidone, polyvinylalcohol, polyoxyethylene copolymers, polyoxypropylene copolymers, polyethyleneoxide, and a mixture thereof.

12. The composition of claim 10, wherein said excipient is selected from the group consisting of a direct compression material and a non-direct compression material.

13. The composition of claim 12, wherein said excipient is selected from the group consisting of a spray-dried mannitol and spray-dried lactose.

14. The composition of claim 1, wherein the solid dose formulation is made by fluid bed granulation.

15. The composition of claim 1 further comprising at least one effervescent agent.

16. The composition of claim 1, wherein said composition has been lyophilized.

17. The composition of claim 1, wherein the poorly soluble active agent is in the form of crystalline particles, semi-crystalline particles, amorphous particles, or a mixture thereof.

18. The composition of claim 1, wherein the effective average particle size of the active agent particles is less than about 1000 nm.

19. The composition of claim 1, wherein the effective average particle size of the active agent particles is less than about 600 nm.

20. The composition of claim 1, wherein the effective average particle size of the active agent particles is less than about 400 nm.

21. The composition of claim 1, wherein the effective average particle size of the active agent particles is less than about 300 nm.

22. The composition of claim 1, wherein the effective average particle size of the active agent particles is less than about 250 nm.

23. The composition of claim 1, wherein the effective average particle size of the active agent particles is less than about 100 nm.

24. The composition of claim 1, wherein the effective average particle size of the active agent particles is less than about 50 nm.

25. A method of preparing an oral solid dose rapidly disintegrating nanoparticulate formulation comprising:
  (a) combining (i) a nanoparticulate composition of a poorly soluble active agent and at least one surface stabilizer adsorbed to the surface thereof, wherein the active agent has an effective average particle size of less than about 2000 nm, and (ii) at least one pharmaceutically acceptable water-dispersible or water-soluble excipient, which forms a solid dose matrix surrounding the nanoparticulate composition; and
  (b) forming a solid dose formulation, wherein the solid dose matrix surrounding the nanoparticulate active agent and surface stabilizer substantially completely disintegrates or dissolves upon contact with saliva in less than about 3 minutes.

26. The method of claim 25, wherein the effective average particle size of the active agent particles is less than about 1500 nm.

27. The method of claim 25, wherein the solid dose matrix substantially completely disintegrates or dissolves upon contact with saliva in a time period selected from the group consisting of less than about 2 minutes, less than about 90 seconds, less than about 60 seconds, less than about 45 seconds, less than about 30 seconds, less than about 20 seconds, less than about 15 seconds, less than about 10 seconds, and less than about 5 seconds.

28. The method of claim 25, wherein the nanoparticulate composition and the at least one water-dispersible or pharmaceutically acceptable water-soluble excipient are combined in step (a) using fluid bed granulation to form granules of the nanoparticulate composition and at least one water-soluble or water-dispersible excipient, which are then compressed in step (b) to form a solid dose formulation.

29. The method of claim 28, comprising adding additional pharmaceutically acceptable water-soluble or water-dispersible excipient to the granules formed by fluid bed granulation in step (a) prior to compression of the granules in step (b) to form a solid dose formulation.

30. The method of claim 25 wherein step (b) comprises compression of the composition formed in step (a).

31. The method of claim 25 wherein step (b) comprises lyophilization of the composition formed in step (a).

32. The method of claim 25 additionally comprising adding at least one effervescent agent to the composition prior to step (b).

33. The method of claim 25, wherein the effective average particle size of the active agent particles is less than about 1000 nm.

34. The method of claim 25, wherein the effective average particle size of the active agent particles is less than about 600 nm.

35. The method of claim 25, wherein the effective average particle size of the active agent particles is less than about 400 nm.

36. The method of claim 25, wherein the effective average particle size of the active agent particles is less than about 300 nm.

37. The method of claim 25, wherein the effective average particle size of the active agent particles is less than about 250 nm.

38. The method of claim 25, wherein the effective average particle size of the active agent particles is less than about 100 nm.

39. The method of claim 25, wherein the effective average particle size of the active agent particles is less than about 50 nm.

40. The method of claim 25, wherein the concentration of the active agent is from about 0.1% to about 99.9% (w/w).

41. The method of claim 40, wherein the concentration of the active agent is from about 5% to about 70% (w/w).

42. The method of claim 41, wherein the concentration of the active agent is from about 15% to about 40% (w/w).

43. The method of claim 25, wherein the concentration of the pharmaceutically acceptable water-soluble or water-dispersible excipient is from about 99.9% to about 0.1% (w/w).

44. The method of claim 43, wherein the concentration of the pharmaceutically acceptable water-soluble or water-dispersible excipient is from about 95% to about 30% (w/w).

45. The method of claim 44, wherein the concentration of the pharmaceutically acceptable water-soluble or water-dispersible excipient is from about 85% to about 60% (w/w).

46. The method of claim 25, wherein said at least one pharmaceutically acceptable water-soluble or water-dispersible excipient is selected from the group consisting of a sugar, a sugar alcohol, a starch, a natural gum, a natural polymer, a synthetic derivative of a natural polymer, a synthetic polymer, and mixtures thereof.

47. The method of claim 46, wherein said at least one pharmaceutically acceptable water-soluble or water-dispersible excipient is selected from the group consisting of lactose, glucose, mannose, mannitol, sorbitol, xylitol, erythritol, lactitol, maltitol, corn starch, potato starch, maize starch, gelatin, carrageenin, acacia, xanthan gum, an alginate, dextran, maltodextran, polyethylene glycol, polyvinylpyrrolidone, polyvinylalcohol, polyoxyethylene copolymers, polyoxypropylene copolymers, polyethyleneoxide, and a mixture thereof.

48. The method of claim 46, wherein said excipient is selected from the group consisting of a direct compression material and a non-direct compression material.

49. The method of claim 48, wherein said excipient is selected from the group consisting of a spray-dried mannitol and spray-dried lactose.

50. The method of claim 25, wherein the poorly soluble active agent is in the form of crystalline particles, semi-crystalline particles, amorphous particles, or a mixture thereof.

51. A method of treating a mammal comprising administering to the mammal an effective amount of a solid dose rapidly disintegrating nanoparticulate formulation wherein:
   (a) the formulation comprises a solid dose matrix comprising at least one pharmaceutically acceptable water-soluble or water-dispersible excipient, and
   (b) within the solid dose matrix a nanoparticulate active agent composition comprising:
      (i) a poorly soluble active agent having an effective average particle size of less than about 2000 nm prior to inclusion in the dosage form; and
      (ii) at least one surface stabilizer adsorbed on the surface of the active agent;
wherein the solid dose matrix surrounding the nanoparticulate active agent and surface stabilizer substantially completely disintegrates or dissolves upon contact with saliva in less than about 3 minutes.

52. The method of claim 51, wherein the effective average particle size of the active agent particles is less than about 1500 nm.

53. The method of claim 51, wherein the effective average particle size of the active agent particles is less than about 1000 nm.

54. The method of claim 51, wherein the effective average particle size of the active agent particles is less than about 600 nm.

55. The method of claim 51, wherein the effective average particle size of the active agent particles is less than about 400 nm.

56. The method of claim 51, wherein the effective average particle size of the active agent particles is less than about 300 nm.

57. The method of claim 51, wherein the effective average particle size of the active agent particles is less than about 250 nm.

58. The method of claim 51, wherein the effective average particle size of the active agent particles is less than about 100 nm.

59. The method of claim 51, wherein the effective average particle size of the active agent particles is less than about 50 nm.

60. The method of claim 51, wherein the concentration of the active agent is from about 0.1% to about 99.9% (w/w).

61. The method of claim 60, wherein the concentration of the active agent is from about 5% to about 70% (w/w).

62. The method of claim 61, wherein the concentration of the active agent is from about 15% to about 40% (w/w).

63. The method of claim 51, wherein the concentration of the pharmaceutically acceptable water-soluble or water-dispersible excipient is from about 99.9% to about 0.1% (w/w).

64. The method of claim 63, wherein the concentration of the pharmaceutically acceptable water-soluble or water-dispersible excipient is from about 95% to about 30% (w/w).

65. The method of claim 64, wherein the concentration of the pharmaceutically acceptable water-soluble or water-dispersible excipient is from about 85% to about 60% (w/w).

66. The method of claim 51, wherein said at least one pharmaceutically acceptable water-soluble or water-dispersible excipient is selected from the group consisting of a sugar, a sugar alcohol, a starch, a natural gum, a natural polymer, a synthetic derivative of a natural polymer, a synthetic polymer, and mixtures thereof.

67. The method of claim 66, wherein said at least one pharmaceutically acceptable water-soluble or water-dispersible excipient is selected from the group consisting of lactose, glucose, mannose, mannitol, sorbitol, xylitol, erythritol, lactitol, maltitol, corn starch, potato starch, maize starch, gelatin, carrageenin, acacia, xanthan gum, an alginate, dextran, maltodextran, polyethylene glycol, polyvinylpyrrolidone, polyvinylalcohol, polyoxyethylene copolymers, polyoxypropylene copolymers, polyethyleneoxide, and a mixture thereof.

68. The method of claim 66, wherein said excipient is selected from the group consisting of a direct compression material and a non-direct compression material.

69. The method of claim 68, wherein said excipient is selected from the group consisting of a spray-dried mannitol and spray-dried lactose.

70. The method of claim 51, wherein the poorly soluble active agent is in the form of crystalline particles, semi-crystalline particles, amorphous particles, or a mixture thereof.

* * * * *

UNITED STATES PATENT AND TRADEMARK OFFICE
CERTIFICATE OF CORRECTION

PATENT NO. : 6,316,029 B1 Page 1 of 1
DATED : November 13 2001
INVENTOR(S) : Rajeev A. Jain et al.

It is certified that error appears in the above-identified patent and that said Letters Patent is hereby corrected as shown below:

<u>Title page,</u>
Item [73] Assignee, replace "Flak Pharma International, Ltd., Shannon (IL)" with
-- Elan Pharma International, Ltd., Shannon (IE). --.

Signed and Sealed this

Twenty-eighth Day of May, 2002

*Attest:*

JAMES E. ROGAN
*Attesting Officer*   *Director of the United States Patent and Trademark Office*